United States Patent [19]

Vanesky et al.

[11] Patent Number: 5,043,529
[45] Date of Patent: Aug. 27, 1991

[54] CONSTRUCTION OF SHIELDED ROOMS USING SEALANTS THAT PREVENT ELECTROMAGNETIC AND MAGNETIC FIELD LEAKAGE

[75] Inventors: Frank W. Vanesky, Vista; David S. Buchanan, Escondido; James R. Marsden, San Diego, all of Calif.

[73] Assignee: Biomagnetic Technologies, Inc., San Diego, Calif.

[21] Appl. No.: 553,112

[22] Filed: Jul. 13, 1990

[51] Int. Cl.⁵ .......................... H05K 9/00; H01S 4/00
[52] U.S. Cl. .......................... 174/35 MS; 174/35 R; 29/593; 29/592.1
[58] Field of Search .......................... 174/35 MS, 35 R; 361/424; 219/10.55 D, 10.55 R; 324/244; 252/500; 29/592.1, 593

[56] References Cited

U.S. PATENT DOCUMENTS

| | | |
|---|---|---|
| 3,013,103 | 12/1961 | Pettler et al. |
| 3,040,118 | 6/1962 | Schaller, Jr. |
| 3,153,692 | 10/1964 | Lindgren |
| 3,217,085 | 11/1965 | Lindgren |
| 3,557,777 | 1/1971 | Cohen |
| 3,608,280 | 9/1971 | Martin |
| 3,745,226 | 7/1973 | Nichols et al. |
| 3,790,696 | 2/1974 | Lindgren |
| 4,490,675 | 12/1984 | Knuettel et al. |
| 4,534,358 | 8/1985 | Young |
| 4,613,820 | 9/1986 | Edelstein |
| 4,651,099 | 3/1987 | Vinegar |
| 4,755,630 | 7/1988 | Smith et al. |
| 4,959,504 | 9/1990 | Yarger et al. |

OTHER PUBLICATIONS

Booklet entitled "Magnetic Shielded Rooms", 5 pages., undated.
Material Safety Data Sheet for Noalox Anti-Oxidant, Mar. 1989.

Primary Examiner—Leo P. Picard
Assistant Examiner—Bot L. Ledynh
Attorney, Agent, or Firm—Gregory O. Garmong

[57] ABSTRACT

A shielded room is constructed with walls having one shell made of electrically conductive facing sheets that prevent penetration of electromagnetic energy into the room, and two shells made of high magnetic permeability facing sheets that prevent penetration of magnetic fields into the room, one within the electrically conductive sheet and one outside the electrically conductive sheet. The edges of the conductive facing sheets are sealed to each other against leakage of electromagnetic energy with a joint compound made of a mixture of electrically conductive metallic particles in a flowable viscous base that enhances the electrical conductivity across the joint and excludes air from the sealed region. To prevent deterioration, the edges of the high magnetic permeability facing sheets are sealed to each other against leakage of magnetic fields with a joint compound made of a mixture of a high magnetic permability material in a flowable viscous base that enhances the "magnetic conductivity" of the joint and excludes air from the sealed region.

14 Claims, 2 Drawing Sheets

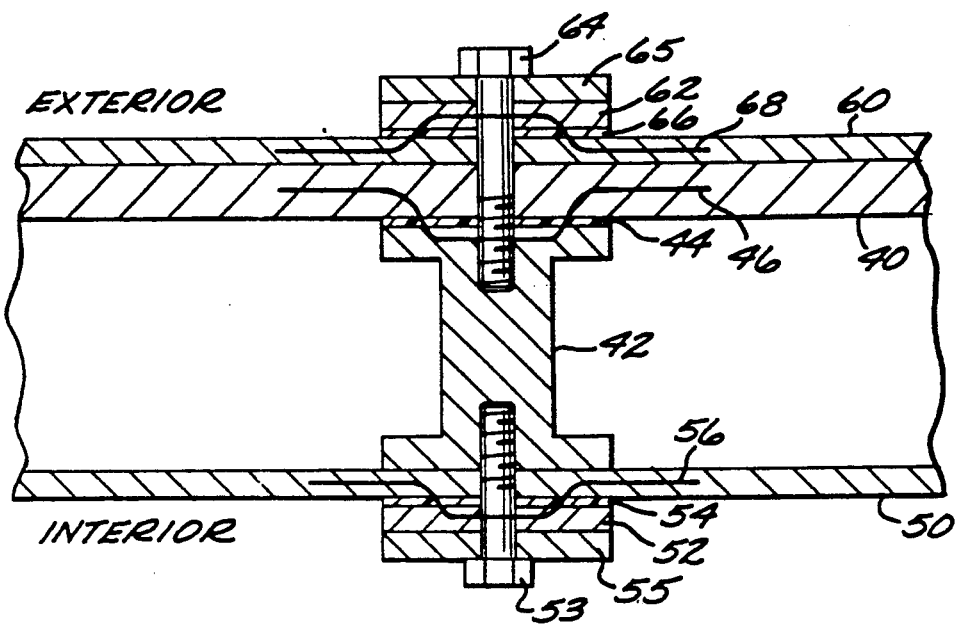
FIG. 4
FIG. 5
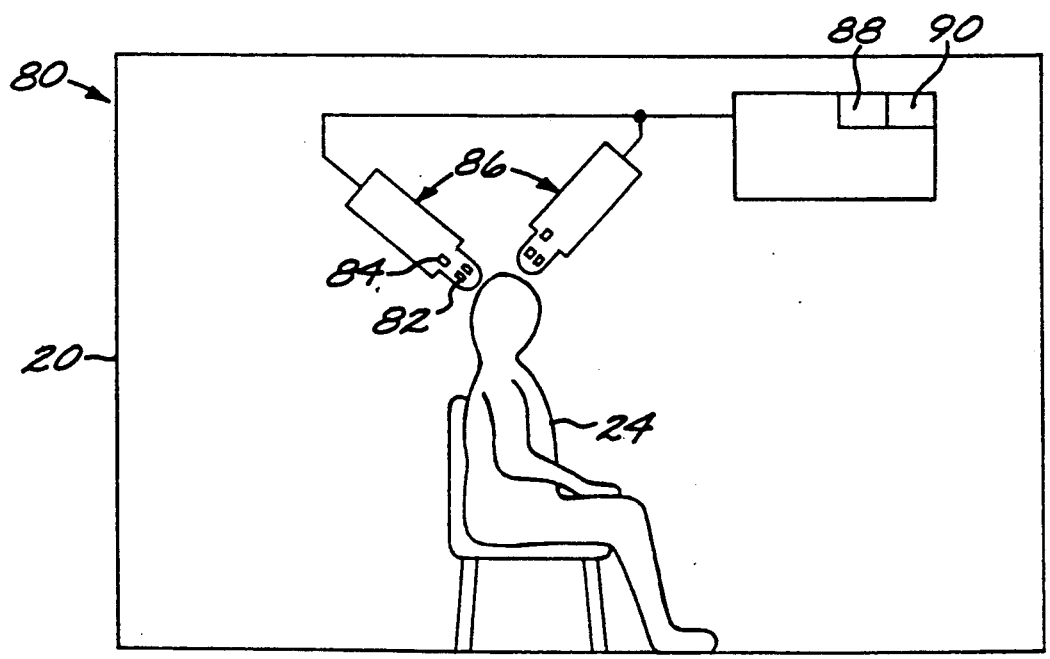

CONSTRUCTION OF SHIELDED ROOMS USING SEALANTS THAT PREVENT ELECTROMAGNETIC AND MAGNETIC FIELD LEAKAGE

BACKGROUND OF THE INVENTION

This invention relates to shielded rooms that produce an internal environment free of external electromagnetic and magnetic fields and to the measurement of biomagnetic fields within such rooms, and, more particularly, to the construction of the rooms.

The biomagnetometer is an instrument that has been developed to measure magnetic fields produced by the body, particularly the brain. The magnetic fields produced by the body are very small and difficult to measure. Typically, the strength of the magnetic field produced by the brain is about 0.00000001 Gauss. By comparison, the strength of the earth's magnetic field is about 0.5 Gauss, or over a million times larger than the strength of the magnetic field of the brain. Most electrical equipment also produced magnetic fields, in many cases much larger than that of the earth. Electromagnetic signals travelling through the environment can also interfere with the taking of magnetic measurements. It is apparent that, unless special precautions are taken, it is difficult or impossible to make magnetic measurements of the human body because the external influences such as the earth's magnetism, nearby apparatus, and electromagnetic signals can completely mask the magnetic fields from the body.

The biomagnetometer includes a very sensitive detector of magnetic signals. The currently most widely used detector is a Superconducting QUantum Interference Device or SQUID, which is sufficiently sensitive to detect magnetic signals produced by the brain. (See, for example. U.S. Pat. Nos. 4,386,361 and 4,403,189, whose disclosures are incorporated by reference, for descriptions of two types of SQUIDs.) This detector and its associated equipment require special operating conditions such as cryogenic temperatures, and cannot be placed into the body or attached directly to the surface of the body.

The present biomagnetometer usually includes a chair or table upon which the patient is positioned, and a structure which supports the SQUID in a cryogenic environment and in proximity with the head of the patient, as about 8 inches away. Special electronics are used to filter out external effects, see for example U.S. Pat. Nos. 3,980,076 and 4,079,730, whose disclosures are herein incorporated by reference. The electronics filters out a portion of the external noise, but in some regimes is not entirely successful. The electronics is also costly and can constitute a major portion of the cost of the system.

There is another possibility for reducing the adverse effect of the external magnetic field, which can be used in place of, or in addition to, the electronic signal processing. In this approach, the patient and detector are placed into a magnetically quiet enclosure that shields the patient and the detector from the external electromagnetic and magnetic fields. The magnitude of the Earth's static magnetic field within the enclosure is reduced from about 0.5 Gauss or more, to less than about 0.001 Gauss. With this reduction in the ambient magnetic field, the biomagnetic events of interest can be measured more readily, and the signal processing required to achieve usable information is greatly reduced.

Magnetically shielded enclosures have been known, as for example the design described in U.S. Pat. No. 3,557,777, whose disclosure is herein incorporated by reference. In this approach, concentric layers of a high permeability metal and a metallic conductor are supported on a frame, thereby forming the walls of the shielded room. To permit construction of the room at remote sites, it is conventional practice to provide the high permeability material and the metallic conductor material as sheets that are assembled to the frame. The '777 patent indicates that the layers of shielding sheets are simply fastened to a wooden frame with screws. While this practice may have been sufficient with the biomagnetic measurement technologies available in the 1960's, current practice with better biomgnetic measurement equipment requires that the interfaces between the sheets must be sealed more positively to prevent field leakage to the interior of the shielded room.

In current construction practice, the edges of the sheets of metallic conductor material are welded to each other to form a continuous shielding surface after assembly to the frame. The welded construction avoids the possibility of leakage of electromagnetic energy through gaps between the sheets, as even a slight leakage can significantly interfere with the current biomagnetic measurements. The sheets of high permeability metal are assembled with large overlaps between the sheets and mechanically fastened, or assembled with small overlaps between the sheets and mechanically clamped. This construction is intended to prevent the leakage of the external magnetic field around the edges of the sheets.

While operable, enclosures having such a partially welded construction cannot be readily disassembled for movement at a later time, as to a new facility. The welding operation must be carefully performed and checked, so that the preparation of each such enclosure is essentially a custom operation, requiring long lead times.

Accordingly, there exists a need for an improved magnetically shielded enclosure which has a low level of electromagnetic and magnetic noise in its interior, the low levels being retained over extended periods of time. Such an enclosure should be capable of being disassembled if necessary, and should be less expensive to construct than existing enclosures. The present invention fulfills this need, and further provides related advantages.

SUMMARY OF THE INVENTION

The present invention provides an approach for constructing a shielded room which can be assembled from prefabricated pieces on site, and if desired at a later time, readily disassembled and reassembled at another site. The room reduces electromagnetic energy and magnetic fields inside the enclosure to acceptably low levels for the making of biomagnetic measurements, without the necessity of welding the structure and at reduced cost as compared with prior types of construction.

In accordance with one aspect of the invention, a shielded room comprises a frame of beams enclosing a volume sufficiently large to admit a person to the interior thereof; a plurality of facing sheets sized to fill the openings between the beams and form the walls of the room, each facing sheet being made of an electrically conductive material; fastener means for mechanically and removably fastening each facing sheet to the beams of the frame along the entire length of each edge of each facing sheet, at least one of the beams and the fastener means being electrically conductive to form a current flow path having mechanical interfaces, between adjacent facing sheets; and a connector seal of a layer of a joint compound along the length of each mechanical interface in the current flow path between two adjacent facing sheets, the joint compound being a mixture of particles of an electrically conductive metal and a flowable base that excludes air from the sealed region. The connector seal of this aspect of the invention permits the first conductive shell that excludes electromagnetic energy to be constructed from facing sheets of conductive material that are removably sealed together, simply by applying the joint compound to the mechanical interfaces as the facing sheets are assembled.

In accordance with another aspect of the invention, a shielded room comprises a room of sufficiently large size to admit a person to the interior thereof and having a wall on each side thereof; a plurality of facing sheets sized to cover the walls of the room, each facing sheet being made of a material with a sufficiently high magnetic permeability to exclude external magnetic fields from the interior of the room, adjacent facing sheets being in contact along a mechanical interface; and a connector seal of a layer of a joint compound along the length of each mechanical interface, the joint compound being a mixture of particles of a material with a sufficiently high magnetic permeability to exclude external magnetic fields from the interior of the room and a flowable base that excludes air from the sealed region. The connector seal of this aspect of the invention permits the shell that excludes magnetic fields to be constructed from facing sheets of high magnetic permeability material that are removably sealed together, simply by applying the joint compound to the mechanical interfaces as the facing sheets are assembled. In the preferred practice, two concentric shells of high permeability material are used, with the edges sealed in the manner indicated.

A material useful as such as sealing compound has not been previously known. In accordance with this aspect of the invention, a joint sealing compound comprises a mixture of particles of a material having a magnetic permeability of at least about 2000, and a flowable base that excludes air from the sealed region, the particles being present in an amount of from about 15 to about 30 percent of the volume of the mixture.

Tests have established that the connector seals for electromagnetic fields and for magnetic fields perform as well as conventional structural joints in excluding interfering fields from the interior of the shielded room.

In the preferred practice, the two connector sealing approaches are used together, the first sheet of conductive material being sealed with the joint compound having conductive particles, and the second sheet of high magnetic permeability material being sealed with the joint compound having high magnetic permeability particles. In the most preferred practice, a third shell of high magnetic permeability is provided and sealed with the joint compound having the high magnetic permeability particles. However, the two approaches need not be used together.

This technique vastly simplifies the construction of shielded rooms at remote sites. The shielded room can be constructed by erecting a frame and attaching the facing sheets that form the two shells to the frame, while sealing the joints with the respective sealing compound as assembly progresses. If at a later time the room is to be disassembled, or if just one facing sheet is to be removed for structural modifications to the room, the disassembly is performed readily with just hand tools. Reassembly of the room or a face sheet is again accomplished with hand tools, with a new coating of the joint compound applied to the sealed edges in the reassembly process.

The approach of the invention permits the shielded room to be completely prefabricated and then assembled at a selected location. Testing has shown that the shielded room achieves satisfactory performance in excluding interfering signals for extended periods of time. The room can later be disassembled for moving or modification, and reassembled with at most the reapplication of the connector seal. Other features and advantages of the invention will be apparent from the following more detailed description of the invention, taken in conjunction with the accompanying drawings, which illustrate, by way of example, the principles of the invention.

BRIEF DESCRIPTION OF THE DRAWINGS

FIG. 4 is a sectional view of the wall of the shielded room of FIG. 1 in its preferred construction, taken along lines 4—4 of FIG. 1, with some diagrammatic elements inserted into the view for explanatory purposes; and FIG. 5 is a schematic depiction of the operation of a biomagnetometer within the shielded room.

DETAILED DESCRIPTION OF THE PREFERRED EMBODIMENTS

Figure 1:
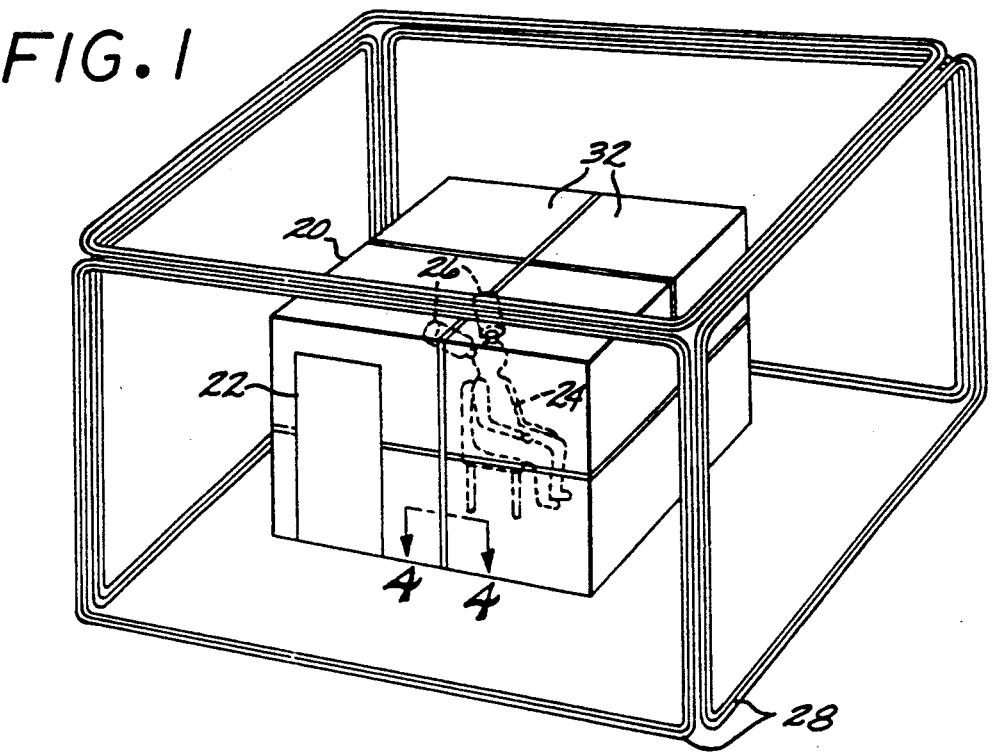
FIG. 1 is a perspective cutaway view of a shielded room utilizing the constructional techniques of the invention.

FIG. 1 illustrates a shielded room 20 having a door 22 therethrough. A person 24 is seated inside the shielded room 20, with two biomagnetometer assemblies 26 positioned for making biomagnetic measurements of the person. An optional three-axis magnetic field cancellation coil 28 is positioned around and outside of the room 20. By way of illustration of the dimensions but not of limitation, the height of the room 20 is typically about 8 feet.

Figure 2:
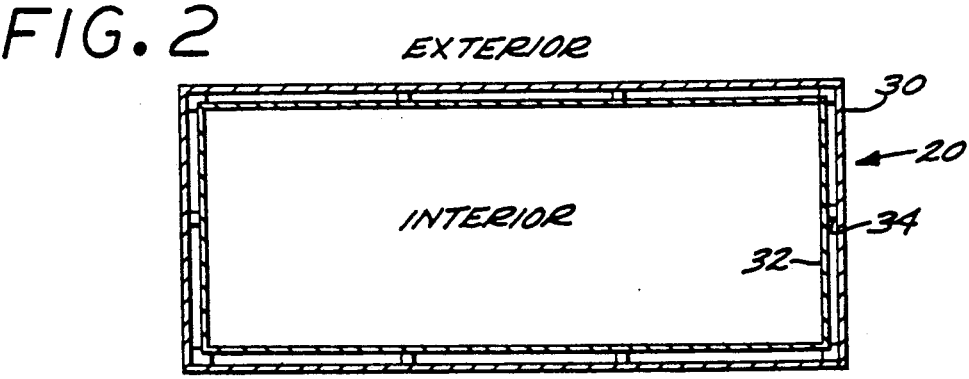
FIG. 2 is a diagrammatic top sectional view of the basic construction of the walls of the shielded room of FIG. 1.

The concept of the construction and operation of the walls of the shielded room 20 is illustrated in FIG. 2. A first shell 30 is formed of an electrically conductive material such as aluminum or and aluminum alloy such as 6061 or 5086 alloy. The first shell 30 extends around the entire perimeter of the room 20 (in three dimensions, including top and bottom as well as the side walls) and excludes electromagnetic energy from the interior of the shielded room 20. A second shell 32 is formed of a material having a sufficiently high magnetic permeability to exclude magnetic fields from the interior of the shielded room 20. The second shell 32 also extends around the entire perimeter of the room 20 (in three dimensions, including top and bottom as well as the side walls). The second shell 32 is preferably formed of mu-metal, a specially processed alloy having a composition of 77 weight percent nickel, 5 weight percent copper, 1.5 weight percent chromium, balance iron. Mu-metal is well known as a magnetic shielding material and is commercially available in processed sheets.

The first shell 30 and the second shell 32 are supported from a frame formed of beams 34. The beams 34 are preferably made of aluminum or aluminum alloy. In the depicted structure, the first shell 30 is supported on the exterior side of the beams 34, and the second shell 34 is supported on the interior side of the beams 34, although this arrangement could be reversed. In an alternative construction, a concentric second electrically conductive shell can be provided.

Figure 3:
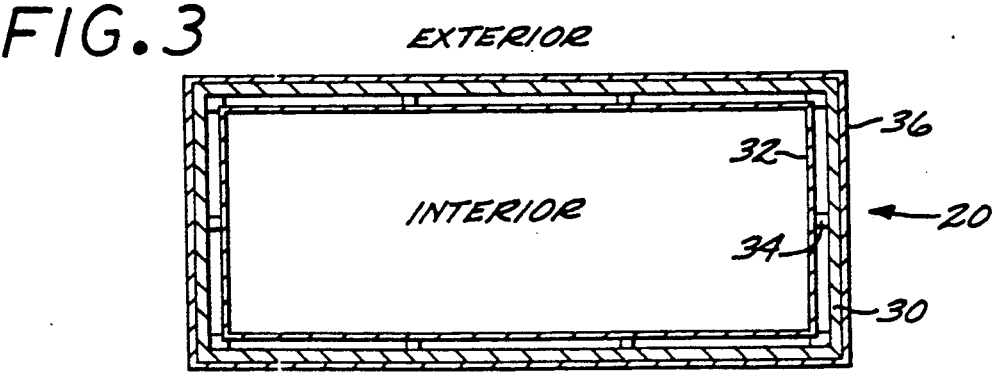
FIG. 3 is a diagrammatic top sectional view of a more preferred construction of the walls of the shielded room of FIG. 1.

FIG. 3 illustrates a modification to the general construction of FIG. 2, the modification being the preferred constructional approach. In this construction, a third shell 36 of high magnetic permeability material, preferably mu-metal, is added to the exterior surface of the shielded room 20. This third shell performs essentially the same function as the second shell 34 in excluding magnetic fields from the interior of the shielded room 20, adding a second layer of protection that serves to reduce even further the magnetic field within the shielded room 20.

By way of illustration and not limitation, in a preferred construction the first shell 30 is made of 6061 or 5086 aluminum alloy that is ⅜ inch thick. If two concentric conductive shells on each side of the beam are used, each is preferably ¼ inch thick. The second shell 32 is made of mu-metal sheet about 0.125 inches thick, and the third shell 36 is made of mu-metal sheet about 0.062 inches thick. The dimension of the beam 34 perpendicular to the shells is about 6 inches, so that the second shell 32 is spaced apart from the first shell 30 by that amount.

If the shells 30, 32, and optionally 36 could be made as a single piece without seams, the present invention would not be necessary. However, it is not possible with present-day technology to form the shells to their final form. In particular, the shells are preferably made of rolled sheet material. These sheets are essentially flat, and are then erected by fastening them to the beams 34 of the frame to form the facings of the room. The natural result of this mode of construction is that there are gaps between the adjacent facing sheets. Even very tiny gaps can permit leakage of electromagnetic energy into the interior of the shielded room 20 in the case of the first shell 30, and leakage of magnetic fields into the interior of the shielded room 20 in the case of the second shell 32 and the third shell 36.

Conventional practice has been to weld the facing sheets of the conductive shells together along their edges to remove these potential leakage paths. Welding of the shells essentially converts the shielded room into a permanent construction, which cannot be readily disassembled and also cannot be readily modified in the sense of removing the facing sheets in one area to modify the shielded room to add instrumentation feed throughs, for example. If the shielded room is disassembled, as by cutting the welds, then reassembly can be difficult because the facing sheets may be warped or slightly of the wrong size after diassembly Conventional practice has been to overlap the facing sheets of the high magnetic permeability material and mechanically fasten the sheets together.

The present invention uses connector seals of joint compounds in the mechanical interfaces between adjacent facing sheets of each shell to prevent leakage paths. Effective joint compound seals of this type have not heretofore been known.

FIG. 4 illustrates the details of the construction of the walls of the shielded room 20 using the approach of the invention. The illustration corresponds to the three-shell construction of FIG. 3, and the construction corresponding to the two-shell construction of FIG. 2 could be accomplished simply by omitting the exterior third shell. It is to be understood that the construction techniques to be described can be used separably for the first shell by itself, the second shelf by itself, the third shell by itself, or together in the manner of the preferred approach. For example, the first shell could be constructed by the approach of the invention, and the second and third shells could be constructed by another approach, and such a technique would still be within the scope of the invention.

In accordance with a first aspect of the invention as applied to the first shell, apparatus for detection of biomagnetic activity of a person comprises a shielded room having means for excluding electromagentic energy from the interior of the room, the means for excluding electromagnetic energy including a plurality of facing sheets of an electrically conductive material with mechanical interfaces between the facing sheets, and a connector seal of a layer of a joint compound along the length of each mechanical interface in the current flow path between two adjacent facing sheets, the joint compound being a mixture of particles of an electrically conductive metal and a flowable base that excludes air from the sealed region, and means for excluding external magnetic fields from the interior of the room; and means for performing measurements of biomagnetic activity of a person located within the room.

In accordance with a second aspect of the invention as applied to either the second shell or the third shell, apparatus for detection of biomagnetic activity of a person, comprises a shielded room having means for excluding electromagnetic energy from the interior of the room, and means for excluding external magnetic fields from the interior of the room, the means for excluding magnetic fields including a plurality of facing sheets of a material with a sufficiently high magnetic permeability to exclude external magnetic fields from the interior of the room with mechanical interfaces between the facing sheets, the mechanical interfaces being sealed with a connector seal of a layer of a joint compound along the length of each mechanical interface, the joint compound being a mixture of particles of a material with a sufficiently high magnetic permeability to exclude external magnetic fields from the interior of the room and a flowable base that excludes air from the sealed region; and means for performing measurements of biomagnetic activity of a person located within the room.

Referring to FIG. 4, the first shell is formed from a plurality of facing sheets 40 of an electrically conductive material, preferably aluminum alloy. By way of illustration and not limitation, facing sheets of about 4 feet by 10 feet dimensions are readily available and can be handled by a rigging crew. The beam arrangement of the frame is determined according to the availability of the facing sheets. The facing sheets 40 are supported on the beams of the frame, here shown as the preferred I-beam 42.

Between each facing sheet 40 and the flange of the I-beam 42 is a layer 44 of a joint compound that acts as a connector seal at the mechanical interfaces between the conductive facing sheet 40 and the I-beam 42. The joint compoind is a mixture of solid particles of an electrically conductive metal and a plastically flowable nonmetallic base that excludes air from the interior of the layer of joint compound. The solid particles are preferably zinc powder having a particle size of about 0.002 inches, in an amount of from about 15 to about 25 percent of the total volume of the joint compound, most preferably about 20 percent of the total volume of the joint compound. If the fraction of particles is too low, the required shielding and conductivity functions are not attained. If the fraction of particles is too high, there is insufficient flowability of the compound wiht the result that cracks that admit air to the interior of the compound may develop.

The base is preferably formed of a mixture of organic species. Preferably, the base is entirely or primarily polybutene, which has a melting point of about 360° F. A lower melting point version can be prepared with petrolatum, also known as petroleum jelly or vaseline, described as entry 6970 of the Merck Index. Petrolatum has a maximum melting point of about 130° F. A mixture of polybutene and petrolatum can also be used. A second component can be added to increase the viscosity of the base, as desired for easy application. The preferred thickener is finely divided silicon dioxide, which is chemically inert in the present application. The silicon dioxide particles are added to the base as necessary to achieve a desirable consistency.

A most preferred version of the joint compound has from 75 to 80 weight percent polybutane, from 0 to 5 weight percent silicon dioxide powder, and about 20 weight percent finely divided zinc. Such a material is available commercially from Ideal Industries, Sycamore, Ill., as it Noalox ® Anti-Oxidant compound.

The viscosity of the preferred joint compound for the layer 44 is slightly greater than the vaseline commonly available in homes. It can be applied by hand or a grease gun apparatus. A bead of the joint compound is applied along the edge of one face of the facing sheet 40 or along the length of the I-beam 42, or both. The bead of joint compound is applied at a location such that, when the facing sheet 40 is pressed against the flange of the I-beam 42 during assembly of the mechanical joint, the bead of joint compound is flattened and squashed between the two pieces. Some of the joint compound may extrude out of the sides of the joint, and can be wiped away.

The function of the base is to act as a carrier for the metallic particles and to exclude air from the interior of the sealed region. When the facing sheet 40 is mechanically clamped tightly against the flange of the I-beam 42, the metallic particles abrade against the aluminum of the facing sheet 40 and the I-beam 42, scraping away aluminum oxide on the aluminum surfaces. The base excludes air that would permit the aluminum oxide layer to reform.

The presence of the layer of joint compound 44 between the conductive facing sheet 40 and the I-beam 42, in cooperation with the conductive I-beam 42 and the conductive facing sheets 40, provides a continuous barrier to the penetration of electromagnetic signals to the interior of the shielded room 20, as indicated schematically in FIG. 4 as a barrier line 46. Tests have shown that the properly applied layer of joint compound 44 excludes electromagnetic energy as effectively as does a welded joint. Moreover, the application of the joint compound is far easier and cheaper to effect than welding. The facing sheets can be readily disassembled and then later reassembled with re-application of the joint compound material.

The second shell 32 is formed of facing sheets 50 of a material that has a high magnetic permeability, preferable mu-metal. These facing sheets 50 are supported by the other flange of the I-beam 42. A clamping bar 52 made of a material having a high magnetic permeability, preferably mu-metal, is clamped against the surface of the facing sheet 50 by the tightening of a fastener 53, which is preferably made of aluminum alloy. A washer 55, preferably made of an aluminum alloy, is placed between the head of the fastener 53 and the clamping bar 52. A connector seal is present in the mechanical interface between the facing sheet 50 and the clamping bar 52 as a layer of a joint compound 54. This layer of joint compound 54, in cooperation with the mu-metal of the facing sheets 50 and the mu-metal of the clamping bar 52, provides a continuous barrier 56 to the penetration of exterior magnetic fields into the interior of the room 20.

The joint compound in the layer 54 is formulated as a mixture of fine particles of a material that has a high magnetic permeability, preferably an alloy of 50 weight percent iron and 50 weight percent nickel, in a flowable base that excludes air from the sealed region. Any material used as the fine particles should have a magnetic permeability of at least about 2000 Gauss/Oersted or greater, to provide the shielding effects required to exclude magnetic flux. The high permeability metal particles are present in an amount of from about 15 to about 30 percent by volume of the mixture, preferably about 20 percent by volume of the mixture. If the amount of metal is substantially below this range, there is an insufficient amount to form the continuous barrier 56. If the amount of the high permeability particles is substantially above this range, the base cannot function properly to form a smooth mixture that is readily applied, and may crack to admit air to the interior of the sealed joint.

The base is preferably of the same preferred composition and composition ranges as the base of the joint compound used for the conductive layer 44 (i.e., polybutene with silicon dioxide added as necessary). It functions in the same manner as described previously for the conductive layer 44.

Testing has demonstrated that the second shell formed in the described manner using the layer of joint compound 54 is equally effective in excluding magnetic fields as prior approaches.

The optional third shell 36 is formed of facing sheets 60 of a high magnetic permeability material, preferably mu-metal. The sheets are clamped to the flange of the I-beam 42 with a mu-metal clamping bar 62 held in place with an aluminum fastener 64 and an intermediate aluminum washer 65. A connector seal material, preferably a layer of joint compound 66 having the same composition as the joint compound 54 used with the second shell, is placed between the facing sheet 60 and the clamping bar 62. In cooperation with the facing sheet 60 and the clamping bar 62, the layer of joint compound 66 forms a barrier 68 to the penetration of any magnetic field into the interior of the shielded room 20. The construction of the third shell 36 is thus substantially the same as the construction of the second shell 32.

The sealants or joint compounds containing electrically conductive or high permeability particles have been demonstrated to have long-term stability in ageing tests. In these tests, the electrical conductivity of joints made using the joint compound having electrically conductive particles, and the magnetic permeability of joints using the joint compound having high permeability particles were measured, and then the joints were subjected to accelerated ageing tests. In these tests, the joints were cycled from 35 C. to 65 C. and back to 35 C. over a four hour period. Each joint was subjected to 104 cycles, with 18 cycles is dry air and 86 cycles in humid air. The performance of the joints was again measured, and in each case there was essentially no deterioration in performance after the ageing tests.

Although not wishing to be bound by this possible explanation, it is believed that the fine particles in the joint compound abrade the joined faces of the respective sheets being joined to a small degree. The abrasion helps scrape away any oxide or other insulator at the face of the sheet, so that a continuous electrically conducting or magnetic field excluding layer is formed through the joint. The base prevents re-oxidation of the abraded regions, in part accounting for the excellent stability against degradation over extended periods of time.

In the preferred approach, the shielded room of the invention is preferably used in conjunction with the making of biomagnetic measurements as shown in FIG. 1 and also FIG. 5. Referring to FIG. 5, a biomagnetometer 80 includes a plurality of magnetic sensing coils 82 for measuring small magnetic fields. The output signal of each magnetic sensing coil 82 is detected by a detector, preferably a superconducting quantum interference device (SQUID) 84. Both the magnetic sensing coil 82 and the SQUID 84 are maintained at a cryogenic operating temperature within a liquid helium dewar 86.

The magnetic signals from the body of the person 24 are picked up by the magnetic sensing coils 82 in the dewar 86, and the signals are detected by the SQUIDs 84. The SQUIDs 84 detect the magnetic field values as electrical currents that are processed in an electronics system 88 and stored in a computer 90 as a function of time, for display and study.

The general structure of the biomagnetometer 26, including the magnetic sensing coils 82, the SQUIDs 84, the dewars 86, the electronics 88, and the computer 90 are known in the art. See for example U.S. Pat. Nos. 4,793,355; 3,980,076, 4,389,612; 4,079,730; 4,386,361; and 4,403,189, whose disclosures are incorporated by reference.

The approach of the invention has the important advantage that the sealing between the sheets of the electromagnetic shielding can be accomplished by a mechanical seal and fastener, so that the room can be readily disassembled and then later reassembled. It is not nesessary to weld the facing sheets together and then later separate them in order to disassemble the room, and then reweld the facing sheet.

Although particular embodiments of the invention has been described in detail for the purpose of illustration, various modifications may be made without departing from the spirit and scope of the invention. Accordingly, the invention is not to be limited except as by the appended claims.

What is claimed is:

1. A shielded room, comprising:
    a frame of beams enclosing a volume sufficiently large to admit a person to the interior thereof;
    a plurality of facing sheets sized to fill the openings between the beams and form the walls of the room, each facing sheet being made of an electrically conductive material;
    fastener means for mechanically and removably fastening each facing sheet to the beams of the frame along the entire length of each edge of each facing sheet, at least one of the beams and the fastener means being electrically conductive to form a current flow path having mechanical interfaces, between adjacent facing sheets; and
    a connector seal of a layer of a joint compound along the length of each mechanical interface in the current flow path between two adjacent facing sheets, the joint compound being a mixture of particles of an electrically conductive metal and a flowable base that excludes air from the sealed region.

2. The shielded room of claim 1, wherein the flowable base of the joint compound includes polybutene.

3. The shielded room of claim 1, wherein the electrically conductive metal of the joint compound is zinc.

4. The shielded room of claim 1, wherein the electrically conductive metal is present in the joint compound in an amount of from about 15 to about 25 percent by volume of the joint compound.

5. A process for excluding electromagnetic energy from the interior of a room, comprising the steps of:
    erecting a room with walls made from facing sheets of an electrically conducting material;
    connecting adjacent facing sheets together with a removable fastener, there being at least one mechanical interface between the two connected facing sheets; and
    interposing a connector seal of a layer of a joint compound along the length of each mechanical interface, the joint compound being a mixture of particles of an electrically conductive metal and a flowable base that excludes air from the sealed region.

6. A shielded room, comprising:
    a room of sufficiently large size to admit a person to the interior thereof and having a wall on each side thereof;
    a plurality of facing sheets sized to cover the walls of the room, each facing sheet being made of a material with a sufficiently high magnetic permeability to exclude external magnetic fields from the interior of the room, adjacent facing sheets being in contact along a mechanical interface; and
    a connector seal of a layer of a joint compound along the length of each mechanical interface, the joint compound being a mixture of particles of a material with a sufficiently high magnetic permeability to exclude external magnetic fields from the interior of the room and a flowable base that excludes air from the sealed region.

7. The shielded room of claim 6, wherein the flowable base includes polybutene.

8. The shielded room of claim 6, wherein the material of high magnetic permeability of the joint compound is an alloy of 50 weight percent iron and 50 weight percent nickel.

9. The shielded room of claim 6, wherein the electrically conductive metal is present in the joint compound in an amount of from about 15 to about 30 percent by volume of the joint compound.

10. A process for excluding magnetic interference from the interior of a room, comprising the steps of:

erecting a room with walls covered with facing sheets of a material having a sufficiently high magnetic permeability to exclude external magnetic fields from the interior of the room, adjacent facing sheets being in contact along a mechanical interface; and interposing a connector seal of a layer of a joint compound along the length of each mechanical interface, the joint compound being a mixture of particles of a material with a sufficiently high magnetic permeability to exclude external magnetic fields from the interior of the room and a flowable base that excludes air from the sealed region.

11. Apparatus for detection of biomagnetic activity of a person, comprising:

a shielded room having means for excluding electromagnetic energy from the interior of the room, the means for excluding electromagnetic energy including a plurality of facing sheets of an electrically conductive material with mechanical interfaces between the facing sheets, and a connector seal of a layer of a joint compound along the length of each mechanical interface in the current flow path between two adjacent facing sheets, the joint compound being a mixture of particles of an electrically conductive metal and a flowable base that excludes air from the sealed region, and means for excluding external magnetic fields from the interior of the room; and means for performing measurements of biomagnetic activity of a person located within the room.

12. The apparatus of claim 11, wherein the means for excluding magnetic fields includes a plurality of facing sheets of a material with a sufficiently high magnetic permeability to exclude external magnetic fields from the interior of the room with mechanical interfaces between the facing sheets, the mechanical interfaces being sealed by a connector seal of a layer of a joint compound along the length of each mechanical interface, the joint compound being a mixture of particles of a material with a sufficently high magnetic permeability to exclude external magnetic fields from the interior of the room and a flowable base that excludes air from the sealed region.

13. Apparatus for detection of biomagnetic activity of a person, comprising:

a shielded room having means for excluding electromagnetic energy from the interior of the room, and means for excluding external magnetic fields from the interior of the room, the means for excluding magnetic fields including a plurality of facing sheets of a material with a sufficiently high magnetic permeability to exclude external magnetic fields from the interior of the room with mechanical interfaces between the facing sheets, the mechanical interfaces being sealed with a connector seal of a layer of a joint compound along the length of each mechanical interface, the joint compound being a mixture of particles of a material with a sufficiently high magnetic permeability to exclude external magnetic fields from the interior of the room and a flowable base that excludes air from the sealed region; and means for performing measurements of biomagnetic activity of a person located within the room.

14. The apparatus of claim 13, wherein the means for excluding electromagnetic energy includes a plurality of facing sheets of an electrically conductive material with mechanical interfaces between the facing sheets, the mechanical interfaces being sealed by a connector seal of a layer of a joint compound along the length of each mechanical interface in the current flow path between two adjacent facing sheets, the joint compound being a mixture of particles of an electrically conductive metal and a flowable base that excludes air from the sealed region.

* * * * *